(12) United States Patent
Lowe, III

(10) Patent No.: US 7,101,881 B2
(45) Date of Patent: Sep. 5, 2006

(54) TETRAHYDROQUINOLINES

(75) Inventor: John Lowe, III, Stonington, CT (US)

(73) Assignee: Pfizer Inc, New York, NY (US)

( * ) Notice: Subject to any disclaimer, the term of this patent is extended or adjusted under 35 U.S.C. 154(b) by 61 days.

(21) Appl. No.: 10/852,726

(22) Filed: May 24, 2004

(65) Prior Publication Data

US 2004/0254193 A1 Dec. 16, 2004

Related U.S. Application Data

(60) Provisional application No. 60/477,559, filed on Jun. 11, 2003.

(51) Int. Cl.
*A61K 31/5377* (2006.01)
*A61K 31/496* (2006.01)
*C07D 401/04* (2006.01)
*C07D 401/14* (2006.01)
*C07D 413/14* (2006.01)

(52) U.S. Cl. .............................. 514/235.2; 514/253.05; 544/121; 544/363

(58) Field of Classification Search ................ 544/121, 544/363; 514/235.2, 253.05
See application file for complete search history.

(56) References Cited

U.S. PATENT DOCUMENTS 6,313,118 B1  11/2001  Berg et al.

FOREIGN PATENT DOCUMENTS

WO  03037887  5/2003

OTHER PUBLICATIONS

K. Rasmussen et al., *Recent Progress in Serotonin (5-HT)$_{1A}$ Receptor Modulators*, Ann. Rap. Med. Chem., 1, 30, 1-9 (1995).
R. Sharma et al., *5-HT 1B Receptor System: Possible Implications for Schizophrenic Negative Symptomatology* Psychiatric Annals, 26, 88-92 (1998).
S. Ramboz, et al., *5-HT1B receptor knock out-behavioral consequences*, Behav. Brain Res., 73, 305-312 (1996).

Primary Examiner—Emily Bernhardt
(74) Attorney, Agent, or Firm—Steve T. Zelson; Mary J. Hosley

(57) ABSTRACT

The present invention relates to compounds of formula I

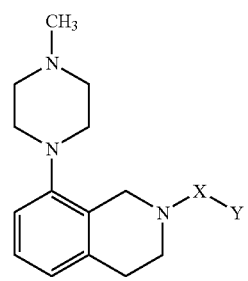

wherein X and Y are as defined in the specification, and to pharmaceutical compositions comprising the compound of formula I and a pharmaceutically effective carrier; and to a method useful in treating or preventing in mammals, including humans, a disorder or condition selected from the group consisting of anxiety, depression, dysthymia, major depressive disorder, migraine, post-traumatic stress disorder, avoidant personality disorder, borderline personality disorder and phobias.

4 Claims, No Drawings

TETRAHYDROQUINOLINES

FIELD OF THE INVENTION

This invention relates to novel tetrahydroquinolines. The invention also relates to pharmaceutical compositions comprising such compounds and to the use thereof in treating diseases or conditions which are caused by disorders of the serotonin system.

BACKGROUND OF THE INVENTION

Serotonin plays a role in several psychiatric disorders, including anxiety, Alzheimer's disease, depression, nausea and vomiting, eating disorders, and migraine. (Rasmussen et al., "Chapter 1. Recent Progress in Serotonin (5HT), Receptor Modulators", in *Annual Reports in Medicinal Chemistry*, Section 1, 30, pp. 1–9, 1995, Academic Press). Serotonin also plays a role in both the positive and negative symptoms of schizophrenia. (Sharma et al., *Psychiatric Annals.*, 26 (2), February, 1996, pp. 88–92.)

Numerous receptor subtypes have been classified according to their antagonist susceptibilities and their affinities for 5HT. The $5HT_{1B}$ receptor was first identified in rats, where it has a distinct pharmacological profile. In humans, however, it shares an almost identical pharmacology with the $5HT_{1D}$ receptor. In the CNS, the receptor is found in the striatum, medulla, hippocampus, frontal cortex and amygdala. In the periphery, it is found in vascular smooth muscle. The $5HT_{1B}/5HT_{1D}$ receptor may be the therapeutic substrate of the anti-migraine drug, sumatriptan; this receptor is also implicated in feeding behavior, anxiety, depression, cardiac function and movement.

Selective agonists and antagonists for $5HT_{1B}$ receptors have until now been lacking, but indirect pharmacological evidence suggests that $5HT_{1B}$ activation influences food intake, sexual activity, locomotion, and aggression. (Ramboz S., et al., *Behav. Brain Res.*, 1996. 73: 305312.).

Accordingly, the compounds of the present invention are antagonists of the serotonin $5HT_{1B}$ receptor, and are effective for the treatment of disorders of the serotonin system, such as depression and related disorders.

SUMMARY OF THE INVENTION

This invention relates to tetrahydroquinolines:

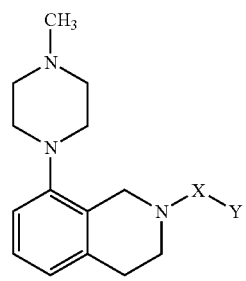

I wherein X is a linker group selected from the group consisting of $CH_2$, $CH_2CH_2$, $C=O$, $C=OCH_2$, $CH_2C=O$, $OCH_2$, $OCH_2CH_2$, $CH_2O$, and $CH_2CH_2O$, and Y is an alkyl or aryl group, wherein the aryl group is selected from phenyl, naphthyl and heteroaryl, wherein said heteroaryl is selected from five to seven membered aromatic rings or eight to ten membered fused aromatic ring systems containing from one to four heteroatoms selected from oxygen, nitrogen and sulfur, and wherein the aryl group may be optionally substituted with one or more substituents, preferably from zero to two substituents, independently selected from halogen, trifluoromethyl, hydroxy, nitro, cyano, $R_1$, $OR_2$, $-OC(=O)R_3$, $-COOR_4$, $NHR_5$, $NR_5R_6$, $-NHC(=O)R_5$, $N(R_5)(C=O)R_6$, $-C(=O)NHR_6$, phenyl, naphthyl, heteroaryl, or a 5 to 7 membered heteroalkyl ring, and wherein said heteroaryl substituent is selected from five to seven membered aromatic rings containing from one to four heteroatoms selected from oxygen, nitrogen and sulfur, and wherein said 5 to 7 membered heteroalkyl ring substituent has from zero to four heteroatoms selected from nitrogen, sulfur and oxygen, with the proviso that said ring cannot contain two adjacent oxygen atoms or two adjacent sulfur atoms, and wherein said phenyl, naphthyl, heteroaryl and heteroalkyl ring substituents may be optionally substituted with one or more substituents, preferably from zero to two substituents, independently selected from halogen, trifluoromethyl, hydroxy, nitro, cyano, $R_1$, $OR_2$, $-OC(=O)R_3$, $-COOR_4$, $NHR_5$, $NR_5R_6$, $-NHC(=O)R_5$, $N(R_5)(C=O)R_6$, $-C(=O)NHR_6$ and wherein said heteroalkyl ring may also be substituted with oxo, wherein each of $R_1$, $R_2$, $R_3$, $R_4$, $R_5$ and $R_6$ is independently selected from the group consisting of alkyl and $C_6$–$C_{14}$ aryl.

The invention is also directed to a compound selected from:

N-(4-Chlorophenylacetyl)-8-(4-methylpiperazinyl)-tetrahydroisoquinoline; 3-(4-Chloro-phenyl)-1-[8-(4-methyl-piperazin-1-yl)-3,4-dihydro-1H-isoquinolin-2-yl]-propan-1-one;

2-(4-Methoxy-phenyl)-1-[8-(4-methyl-piperazin-1-yl)-3,4-dihydro-1H-isoquinolin-2-yl]-ethanone;

1-[8-(4-Methyl-piperazin-1-yl)-3,4-dihydro-1H-isoquinolin-2-yl]-2-p-tolyl-ethanone; 2-(4-Chloro-phenoxy)-1-[8-(4-methyl-piperazin-1-yl)-3,4-dihydro-1H-isoquinolin-2-yl]-ethanone; 2-(2,4-Dichloro-phenyl)-1-[8-(4-methyl-piperazin-1-yl)-3,4-dihydro-1H-isoquinolin-2-yl]-ethanone;

2-(2-Chloro-phenyl)-1-[8-(4-methyl-piperazin-1-yl)-3,4-dihydro-1H-isoquinolin-2-yl]-ethanone;

2-Cyclopropyl-1-[8-(4-methyl-piperazin-1-yl)-3,4-dihydro-1H-isoquinolin-2-yl]-ethanone;

1-[8-(4-Methyl-piperazin-1-yl)-3,4-dihydro-1H-isoquinolin-2-yl]-2-pyridin-3-yl-ethanone;

(4-Chloro-phenyl)-[8-(4-methyl-piperazin-1-yl)-3,4-dihydro-1H-isoquinolin-2-yl]-methanone;

[8-(4-Methyl-piperazin-1-yl)-3,4-dihydro-1H-isoquinolin-2-yl]-(4-morpholin-4-yl-phenyl)-methanone;

2-(3,4-Dichloro-phenyl)-1-[8-(4-methyl-piperazin-1-yl)-3,4-dihydro-1H-isoquinolin-2-yl]-ethanone; and 2-(4-Chloro-benzenesulfonyl)-8-(4-methyl-piperazin-1-yl)-1,2,3,4-tetrahydroisoquinoline.

The invention is also directed to pharmaceutical compositions comprising the compound of Formula I and a pharmaceutically effective carrier.

The invention is also directed to a method of treating or preventing a disorder or condition that can be treated or prevented by altering serotonin-mediated neurotransmission in a mammal, including a human comprising administering to a mammal or human in need of such treatment an effective amount of the compound of Formula I or a pharmaceutically acceptable salt thereof.

The invention is also directed to a method of treating, in a mammal, including a human, a disorder or condition selected from the group consisting of anxiety, depression, dysthymia, major depressive disorder, migraine, post-traumatic stress disorder, avoidant personality disorder, borderline personality disorder and phobias comprising administering to a mammal or human in need of such treatment an effective amount of the compound of Formula I or a pharmaceutically acceptable salt thereof.

The invention is also directed to any of the foregoing methods wherein the compound of Formula I, or a pharmaceutically acceptable salt thereof, is administered in combination with a serotonin reuptake inhibitor (SRI) (e.g., sertraline, fluoxetine, fenfluramine, or fluvoxamine). The term "administered in combination with," as used herein, means that the compound of Formula I or pharmaceutically acceptable salt thereof is administered in the form of a pharmaceutical composition that also contains an SRI, or that such compound or salt is administered in a separate pharmaceutical composition from that in which the SRI is administered, but as part of a dose regimen that calls for the administration of both active agents for treatment of a particular disorder or condition.

The pharmaceutically acceptable acid addition salts of compounds of the Formula I may be used, as referred to above, in the various methods of this invention. The compounds of Formula I are basic in nature and are thus capable of forming a wide variety of salts with various inorganic and organic acids. The acids that may be used to prepare pharmaceutically acceptable acid addition salts of those compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

The term "one or more substituents", as used herein, includes from one to the maximum number of substituents possible based on the number of available bonding sites.

The term "disorders of the serotonin system", as used herein, refers to disorders the treatment of which can be effected or facilitated by altering (i.e., increasing or decreasing) serotonin-mediated neurotransmission.

The term "treating", as used herein, refers to retarding or reversing the progress of, or alleviating or preventing either the disorder or condition to which the term "treating" applies, or one or more symptoms of such disorder or condition. The term "treatment", as used herein, refers to the act of treating a disorder or condition, as the term "treating" is defined above.

The term "treatment effective amount," as used herein, refers to an amount sufficient to detectably treat, ameliorate, prevent or detectably retard the progression of an unwanted condition or symptom associated with disorders of the serotonin system.

The chemist of ordinary skill will recognize that certain combinations of substituents included within the scope of formula I may be chemically unstable and will avoid these combinations or alternatively protect sensitive groups with well known protecting groups.

The term "alkyl", as used herein, unless otherwise indicated, includes saturated monovalent hydrocarbon radicals with 1–12 carbon atoms having straight, branched or cyclic moieties or combinations thereof. The term "lower alkyl" refers to an alkyl group having one to six carbon atoms. Examples include methyl, ethyl, propyl, isopropyl, cyclopropyl, butyl, isobutyl, sec-butyl, t-butyl, pentyl, neopentyl, cyclopentylmethyl, and hexyl. It is preferred that the alkyl group is lower alkyl. The preferred lower alkyl group contains 1–3 carbon atoms. The most preferred alkyl group is methyl.

The term "alkoxy", as used herein, unless otherwise indicated, refers to radicals having the formula —O-alkyl, wherein "alkyl" is defined as above. As used herein, the term "lower alkoxy" refers to an alkoxy group having 1–6 carbon atoms. It may be straight chain or branched. Examples include methoxy, ethoxy, propoxy, isopropoxy, butoxy, isobutoxy, pentoxy and the like. It is preferred that alkoxy is lower alkoxy. It is more preferred that alkoxy contains 1–3 carbon atoms. The most preferred alkoxy group is methoxy.

The halogen atoms contemplated by the present invention are F, Cl, Br, and I. Chlorine and fluorine are preferred. Alkyl groups substituted with one or more halogen atoms include chloromethyl, 2,3-dichloropropyl, and trifluoromethyl. It is preferred that the halo groups are the same. The most preferred is trifluoromethyl.

The term "alkenyl" as used herein refers to a hydrocarbon radical with two to eight carbon atoms and at least one double bond. The alkenyl group may be straight-chained, branched, or cyclic, and may be in either the Z or E form. Examples include ethenyl, 1-propenyl, 2-propenyl, 1-butenyl, 2-butenyl, isopropenyl, isobutenyl, 1-pentenyl, (Z)-2-pentenyl, (E)-2-pentenyl, (Z)-4-methyl-2-pentenyl, (E)-4-methyl-2-pentenyl, 1,3-pentadienyl, 2,4-pentadienyl, 1,3-butadienyl, cyclopentadienyl, and the like. The preferred alkenyl group is ethenyl.

The term "alkynyl" refers to a hydrocarbon radical with two to eight carbon atoms and at least one carbon-carbon triple bond. The alkynyl group may be straight chained or branched. Examples include 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl, and the like. The preferred alkynyl group is ethynyl.

The term "aryl", as used herein, unless otherwise indicated, includes an organic radical derived from a $C_6$–$C_{14}$ aromatic hydrocarbon by removal of one or more hydrogen(s). Examples include phenyl and naphthyl.

The term "heteroaryl", as used herein, unless otherwise indicated, includes an organic radical derived from an aromatic heterocyclic compound by removal of one or more hydrogens. Examples of heteroaryl groups include benzimidazolyl, benzofuranyl, benzofurazanyl, 2H-1-benzopyranyl, benzothiadiazine, benzothiazinyl, benzothiazolyl, benothiophenyl, benzoxazolyl, furazanyl, furopyridinyl, furyl, imidazolyl, indazolyl, indolinyl, indolizinyl, indolyl, 3H-indolyl, isiondolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl or pyridyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl.

The term "heterocyclic compound" denotes a ring system made up of 5–14 ring atoms and made up of carbon and at least one other element selected from the group consisting of oxygen, nitrogen, and sulfur.

The term "5 to 7 membered heteroalkyl ring" includes pyrrolidinyl, piperidyl, piperazinyl, morpholinyl, thiomorpholinyl, diazepinyl, oxazepinyl, thiazepinyl, oxadiazepinyl, thiadiazepinyl or triazepinyl, as well as compounds having one or more carbonyl groups within the ring such as pyrrolidin-2-one and piperidin-2-one.

The compounds of Formula I contain one or more chiral centers and therefore exist in different enentiomeric and diastereomeric forms. Formula I, as defined above, includes—and this invention relates to the use of—all optical isomers and other stereoisomers of compounds of the Formula I and mixtures thereof.

5HT receptor ligands are of clinical use in the treatment of a wide variety of disorders related to serotonin-mediated physiological pathways.

This invention is also directed to a method of treating a disorder or condition that can be treated by altering (i.e., increasing or decreasing) serotonin-mediated neurotransmission in a mammal, including a human, comprising administering to said mammal an amount of a compound of the Formula I, as defined above, or a pharmaceutically acceptable salt thereof, that is effective in treating such disorder or condition.

This invention is also directed to a method of treating migraine, headache or cluster headache in a mammal, including a human, comprising administering to said mammal an amount of a compound of the Formula I, as defined above, or a pharmaceutically acceptable salt thereof, that is effective in treating such disorder.

This invention is also directed to a method of treating a disorder selected from, depression (i.e., dysthymia, major depressive disorder, pediatric depression, recurrent depression, single episode depression, post partum depression, depression in Parkinson's patients, cancer patients, and post myocardial infarction patients, and subsyndromal symptomatic depression) generalized anxiety disorder, panic disorder, obsessive-compulsive disorder, post-traumatic stress disorder, avoidant personality disorder, borderline personality disorder and phobias in a mammal, including a human, comprising administering to said mammal an amount of a compound of the formula I, as defined above, or a pharmaceutically acceptable salt thereof, that is effective in treating such disorder.

Formula I above includes compounds identical to those depicted but for the fact that one or more atoms (for example, hydrogen, carbon or fluorine atoms) are replaced by radioactive isotopes thereof. Such radiolabeled compounds are useful as research and diagnostic tools in, for example, metabolism studies, pharmacokinetic studies and binding assays.

This invention is also directed to a method, such as positron emission tomography (PET), of obtaining images of a mammal, including a human, to which a radiolabeled compound of the Formula I, or pharmaceutically acceptable salt thereof, has been administered. Such imaging methods can potentially be used for any organ or system in which the $5\text{-HT}_{1B}$ receptor is found, such as those indicated above. The utility of radioactive agents with affinity for 5HT receptors for visualizing organs of the body either directly or indirectly has been documented in the literature. For example, C.-Y. Shiue et al., *Synapse*, 1997, 25, 147 and S. Houle et al., *Can. Nucl. Med. Commun.*, 1997, 18, 1130, describe the use of $5\text{HT}_{1A}$ receptor ligands to image $5\text{HT}_{1A}$ receptors in the human brain using positron emission tomography (PET). The foregoing references are incorporated herein by reference in their entireties.

DETAILED DESCRIPTION OF THE INVENTION

An exemplary embodiment of this invention is an embodiment where the linker group X is $CH_2$, $CH_2CH_2$, $C=O$, $CH_2C=O$, $OCH_2$, $OCH_2CH_2$, $CH_2O$, or $CH_2CH_2O$.

For example, X may be CO, as illustrated in Scheme 1 below. Another exemplary embodiment of this invention is an embodiment where the substituent or substituents on the phenyl, naphthyl, heteroaryl or heteroalkyl ring are independently halogen, trifluoromethyl, hydroxy, nitro, cyano, $OR_2$, $-OC(=O)R_3$, $-COOR_4$, $NHR_5$, $NR_5R_6$, $-NHC(=O)R_5$, $N(R_5)(C=O)R_6$, or $-C(=O)NHR_6$.

The compounds of formula I can be prepared according to the methods of Scheme 1. Except where otherwise stated, Ar, Y, Z, a and n in the reaction schemes and discussion that follow are defined as above. Unless otherwise stated reaction conditions include an inert atmosphere commonly used in the art such as nitrogen or argon.

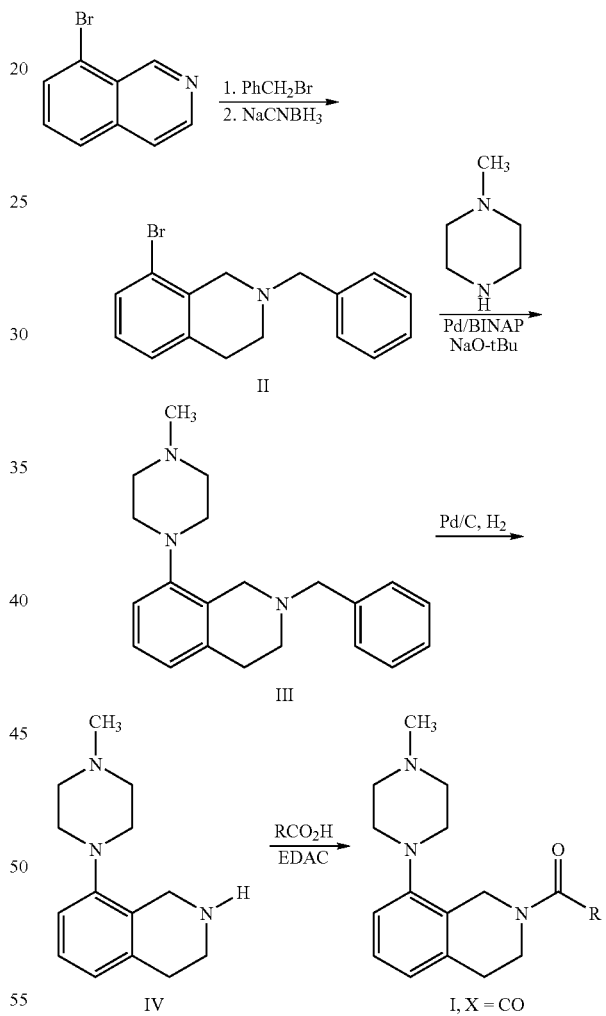

Scheme 1 refers to the preparation of a compound of the formula I wherein X is CO. In step 1 of Scheme 1, 8-bromo-isoquinoline is alkylated with benzyl bromide using a solvent such as acetonitrile, tetrahydrofuran, N-methylpyrrolidinone, dimethylformamide, or an ethereal or chlorinated hydrocarbon solvent; for 1 to 48 hours, at room temperature to reflux. The resulting intermediate is reduced with sodium borohydride, sodium cyanoborohydride, or sodium triacetoxyborohydride, in an ethereal solvent such as tetrahydrofuran, dioxane, or ethyl ether, chlorinated hydrocarbons such as methylene chloride or 1,2-dichloroethane, or an alcoholic solvent such as methanol or ethanol, at room temperature to reflux.

In Step 2, intermediate II is treated with N-methylpiperazine in the presence of a palladium catalyst such as palladium acetate or dibenzylidene acetone palladium, BINAP, and a strong base such as sodium t-butoxide or another metal alkaline metal alkoxide, in a hydrocarbon solvent such as toluene or heptane, or an ethereal solvent such as dioxane, at room temperature to reflux, for 1 to 48 hours.

In Step 3, intermediate III is hydrogenated using palladium or platinum as a catalyst under hydrogen at atmospheric to 3 atmospheres pressure, in a solvent such as an alcohol such as methanol or ethanol, or an ethereal solvent such as tetrahydrofuran or dioxane, or a hydrocarbon solvent such as toluene, or ethyl acetate, for 1 to 48 hours at room temperature to 80° C.

In step 4, intermediate IV is converted to final product I by acetylation using an acid in the presence of a condensing agent such as EDAC or DCC, with a mild base such as an organic base such as triethylamine or diisopropylethyl amine, in a solvent such as an ethereal solvent such as ethyl ether, dioxane ot tetrahydrofuran, a chlorinated hydrocarbon such as methylene chloride or 1,2-dichloroethane, dimethylformamide, N-methylpyrrolidinone, or toluene, at room temperature to reflux, for 1 to 48 hours.

Compounds of formula I may be converted into pharmaceutically acceptable salts by methods well known to those skilled in the art.

Compounds of Formula I in which one or more atoms are radioactive may be prepared by methods known to a person of ordinary skill in the art. For example, compounds of Formula I wherein the radioactive atom is tritium may be prepared by reacting an aryl halide Ar-X, wherein the halogen is chlorine, bromine or iodine, with gaseous $^3H_2$ and a noble metal catalyst, such as palladium suspended on carbon, in a suitable solvent such as a lower alcohol, preferably methanol or ethanol. Compounds of Formula I wherein the radioactive atom is $^{18}F$ may be prepared by reacting an aryl trialkyl stannane Ar—SnR$_3$, wherein R is lower alkyl, preferably methyl or n-butyl, with $^{18}F$-enriched fluorine (F$_2$), OF$_2$ or CF$_3$COOH in a suitably inert solvent (cf M. Namavari, et al., *J. Fluorine Chem.*, 1995, 74, 113).

Compounds of Formula I wherein the radioactive atom is $^{14}C$ may be prepared by reacting an aryl halide Ar-X, wherein X is preferably bromine or iodine, or an aryl trifluoromethane sulfonate (Ar-OSO$_2$CF$_3$) with potassium [$^{14}C$]cyanide or potassium [$^{14}C$]-cyanide and a noble metal catalyst, preferably tetra-kis(triphenylphosphine)palladium, in a reaction inert solvent such water or tetrahydrofuran, and preferably a mixture of water and tetrahydrofuran. (See Y Andersson, B. Langstrom, *J. Chem. Soc. Perkin Trans.* 1, 1994, 1395).

The therapeutic compounds used in the methods of this invention can be administered orally, buccally, trans-dermally (e.g., through the use of a patch), parenterally or topically. Oral administration is preferred. In general, these compounds are most desirably administered in dosages ranging from about 1 mg to about 1000 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout.

When used in the same oral, parenteral or buccal pharmaceutical composition as an SRI, the daily dose of the compound of formula I or pharmaceutically acceptable salt thereof will be within the same general range as specified above for the administration of such compound or salt as a single active agent. The daily dose of the SRI in such a composition will generally be within the range of about 1 mg to about 1000 mg.

The therapeutic compounds used in the methods of this invention may be administered alone or in combination with pharmaceutically acceptable carriers or diluents by either of the two routes previously indicated, and such administration may be carried out in single or multiple doses. More particularly, the therapeutic compounds used in the methods of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound used in the methods of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

The activity of the compounds of the present invention with respect to $5HT_{1B}$ (formerly $5HT_{1D}$) binding ability can be determined using standard radioligand binding assays as described in the literature. The $5\text{-}HT_{1A}$ affinity can be measured using the procedure of Hoyer et al. (Brain Res., 376, 85 (1986)). The $5\text{-}HT_{1D}$ affinity can be measured using the procedure of Heuring and Peroutka (J. Neurosci., 7, 894 (1987)).

The in vitro activity of the compounds of the present invention at the $5\text{-}HT_{1D}$ binding site may be determined according to the following procedure. Bovine caudate tissue is homogenized and suspended in 20 volumes of a buffer containing 50 mM TRIS.hydrochloride (tris[hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 µM pargyline and 4 mM calcium chloride ($CaCl_2$). The suspension is kept on ice at least 30 minutes prior to use.

The inhibitor, control or vehicle is then incubated according to the following procedure. To 50 µl of a 20 percent dimethylsulfoxide (DMSO)/80 percent distilled water solution is added 200 µl of tritiated 5-hydroxytryptamine (2 nM) in a buffer of 50 mM TRIS.hydrochloride containing 0.01 percent ascorbic acid at pH 7.7 and also containing 10 µM pargyline and 4 µM calcium chloride, plus 100 nM of 8-hydroxy-DPAT (dipropylaminotetraline) and 100 nM of mesulergine. To this mixture is added 750 µl of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters.™.). The pellet is then washed three times with 4 ml of a buffer of 50 mM TRIS.hydrochloride at pH 7.7. The pellet is then placed in a scintillation vial with 5 ml of scintillation fluid (aquasol 2™) and allowed to sit overnight. The percent inhibition can be calculated for each dose of the compound. An $IC_{50}$ value can then be calculated from the percent inhibition values.

The activity of the compounds of the present invention for $5-HT_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900G for 10 minutes and the supernate separated and recentrifuged at 70,000 G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 µm pargyline and kept on ice.

The tissue is then incubated according to the following procedure. Fifty microliters of control, inhibitor, or vehicle (1 percent DMSO final concentration) is prepared at various dosages. To this solution is added 200 µl of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 µl of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. $IC_{50}$ values are calculated from the percent inhibition values.

The compounds of formula I of the present invention described in the following Examples were assayed for $5-HT_{1A}$ and $5-HT_{1D}$ affinity using the aforementioned procedures. All such compounds of the invention that were tested exhibited $IC_{50}$'s less than 0.60 µM for $5-HT_{1D}$ affinity and $IC_{50}$'s less than 1.0 µM for $5-HT_{1A}$ affinity.

The agonist and antagonist activities of the compounds of the invention at $5-HT_{1A}$ and $5-HT_{1D}$ receptors can be determined using a single saturating concentration according to the following procedure. Male Hartley guinea pigs are decapitated and $5-HT_{1A}$ receptors are dissected out of the hippocampus, while $5-HT_{1D}$ receptors are obtained by slicing at 350 mM on a Mcilwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 µM GTP and 0.5–1 microcuries of [$^{32}P$]-ATP (30 Ci/mmol: NEG-003—New England Nuclear). Incubation is initiated by the addition of tissue to siliconized microfuge tubes (in triplicate) at 30° C. for 15 minutes. Each tube receives 20 µL tissue, 10 µL drug or buffer (at 10× final concentration), 10 µL 32 nM agonist or buffer (at 10× final concentration), 20 µL forskolin (3 µM final concentration) and 40 µL of the preceding reaction mix. Incubation is terminated by the addition of 100 µL 2% SDS, 1.3 mM cAMP, 45 mM ATP solution containing 40,000 dpm [3H]-cAMP (30 Ci/mmol: NET-275—New England Nuclear) to monitor the recovery of cAMP from the columns. The separation of [$^{32}P$]-ATP and [$^{32}P$]-cAMP is accomplished using the method of Salomon et al., Analytical Biochemistry, 1974, 58, 541–548. Radioactivity is quantified by liquid scintillation counting. Maximal inhibition is defined by 10 µM (R)-8-OH-DPAT for $5-HT_{1A}$ receptors, and 320 nM 5-HT for $5-HT_{1D}$ receptors. Percent inhibitions by the test compounds are then calculated in relation to the inhibitory effect of (R)-8-OH-DPAT for $5-HT_{1A}$ receptors or 5-HT for $5-HT_{1D}$ receptors. The reversal of agonist induced inhibition of forskolin-stimulated adenylate cyclase activity is calculated in relation to the 32 nM agonist effect.

The compounds of the invention can be tested for in vivo activity for antagonism of $5-HT_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a $5-HT_{1D}$ agonist, such as [3-(1-methylpyrrolidin-2-ylmethyl)-1H-indol-5-yl]-(3-nitropyridin-3-yl)-amine, which can be prepared as described in PCT publication WO93/11106, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT$_{1D}$ agonist is then administered at 0 minutes and temperatures are taken 30, 60, 120 and 240 minutes later. In subcutaneous screening experiments, a pre-drug baseline temperature reading is made at −30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip (P. P. A. Humphrey et al., Br. J. Pharmacol., 94, 1128 (1988)). This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., Br. J. Pharmacol., 96, 83 (1989).

The serotonin 5-HT$_1$ agonist activity can be determined by the in vitro receptor binding assays, as described for the 5-HT$_{1A}$ receptor using rat cortex as the receptor source and [$^3$H]-8-OH-DPAT as the radioligand (D. Hoyer et al. Eur. J. Pharm., 118, 13 (1985)) and as described for the 5-HT$_{1D}$ receptor using bovine caudate as the receptor source and [$^3$H]serotonin as the radioligand (R. E. Heuring and S. J. Peroutka, J. Neuroscience, 7, 894 (1987)). Of the active compounds tested, all exhibited an IC$_{50}$ in either assay of 1 μM or less.

The following Examples illustrate the preparation of the compounds of the invention.

EXAMPLE 1

N-(4-Chlorophenylacetyl)-8-(4-methylpiperazinyl)-tetrahydroisoquinoline

A. N-Benzyl-8-bromo-tetrahydroisoquinoline: According to Scheme 1: To a 100 mL round-bottomed flask equipped with condenser and N$_2$ inlet were added 2.46 g (11.8 mmol) 8-bromoisoquinoline, 1.68 mL (14.1 mmol) benzyl bromide, and 10 mL ethanol. The solution was heated at reflux for 6 hr, cooled, and evaporated. The oil was dissolved in 50 mL methanol, and 1.73 g (27.6 mmol) sodium cyanoborohydride was added. The solution was stirred at room temperature for 5 days, then diluted with water and extracted with three portions of ethyl acetate. The organic layer was washed with brine, dried over sodium sulfate, and evaporated. The residue was chromatographed on silica gel using hexane/ethyl acetate to afford 1.98 g (59%) of an oil.

$^1$H-NMR (δ, CDCl$_3$): 2.68 (m, 2H), 2.88 (m, 2H), 3.68 (m, 2H), 3.75 (m, 2H), 7.0–7.1 (m, 2H), 7.2–7.4 (m, 6H). $^{13}$C-NMR (δ, CDCl$_3$): MS APCI: 302/304 (P+1, parent, Br$^{79}$/Br$^{81}$).

B. N-Benzyl-8-(4-methylpiperazinyl)-tetrahydroisoquinoline: To a 15 mL round-bottomed flask equipped with condenser and N$_2$ inlet were added 237 mg (0.787 mmol) N-benzyl-8-bromo-tetrahydroisoquinoline, 0.435 mL (3.92 mmol) N-methylpiperazine, 8 mg (0.039 mmol) palladium (II) acetate, 24 mg (0.039 mmol) BINAP, 100 mg (0.944 mmol) sodium t-butoxide, and 5 mL dry toluene. The reaction was heated to 120° C. for 16 hr, during which it changed from red to orange to yellow to gray. The reaction was cooled, diluted with ethyl acetate, washed with water and brine, dried over sodium sulfate, and evaporated. The residue was chromatographed on silica gel using ethyl acetate/methanol/ammonium hydroxide as eluant to afford the product as an oil, 211 mg (84%).

$^1$H-NMR (δ, CDCl$_3$): 2.32 (s, 3H), 2.48 (broad m, 4H), 2.66 (t, J=6, 2H), 2.86 (m, 6H), 3.64 (m, 2H), 3.69 (m, 2H), 6.83 (d, J=7, 1H), 6.88 (d, J=8, 1H), 7.09 (t, J=8, 1H), 7.2–7.4 (m, 5H). $^{13}$C-NMR (δ, CDCl$_3$): 29.58, 46.39, 50.38, 52.17, 53.21, 55.86, 63.11, 117.09, 124.43, 126.75, 127.27, 128.44, 129.47, 130.52, 135.68, 138.68, 150.21. MS APCI: 322 (P+1, parent).

C. 8-(4-Methylpiperazinyl)-tetrahydroisoquinoline: To a Parr bottle were added 174 mg (0.54 mmol) N-benzyl-8-(4-methylpiperazinyl)-tetrahydroisoquinoline, 20 mg (20% palladium hydroxide on carbon, 2 drops concentrated hydrochloric acid, and 20 mL methanol. The mixture was shaken under 30 p.s.i. hydrogen for 9 hr, filtered through Celite®, and the filtrate evaporated. The residue was treated with 1 N aqueous sodium hydroxide and extracted with 3 portions of methylene chloride to afford 100 mg of an oil which was used directly.

$^1$H-NMR (δ, CDCl$_3$): 2.95 (s, 3H), 3.14 (m, 6H), 3.27 (m, 2H), 3.31 (m, 4H), 4.40 (s, 2H), 7.08 (d, J=8, 1H), 7.16 (d, J=8, 1H), 7.32 (t, J=8, 1H).

D. N-(4-Chlorophenylacetyl)-8-(4-methylpiperazinyl)-tetrahydroisoquinoline: To a 15 mL round-bottomed flask equipped with condenser and N$_2$ inlet were added 117 mg (0.50 mmol) 8-(4-methylpiperazinyl)-tetrahydroisoquinoline, 130 mg (0.76 mmol) 4-chlorophenylacetic acid, 105 mg (0.55 mmol) EDAC, 122 mg (0.80 mmol) N-hydroxybenzotriazole, and 4 mL dry methylene chloride. The reaction was stirred at room temperature for 14 hr, diluted with methylene chloride, and washed with dilute aqueous sodium hydroxide solution and brine, dried over sodium sulfate, and evaporated. The residue was chromatographed on silica gel using ethyl acetate/methanol/ammonium hydroxide as eluant to afford the product as an oil, which was converted to the HCl salt, mp 80° C. (dec.).

$^1$H-NMR (δ, CDCl$_3$): 2.33 and 2.35 (singlets, 3H), 2.4–2.6 (broad m, 4H), 2.8–3.0 (m, 6H), 3.61 (t, J=6) and 3.71 singlet (2H), 3.77 (m, 2H), 4.51 and 4.71 (singlets, 2H), 6.8–6.9 (m, 1H), 6.9–7.0 (m, 1H), 7.1–7.3 (m, 6H). $^{13}$C-NMR (δ, CDCl$_3$): 28.71, 29.89, 40.46, 40.67, 41.20, 41.29, 43.78, 44.46, 46.20, 46.42, 52.32, 52.46, 55.60, 55.90, 117.95, 118.19, 123.79, 124.62, 127.44, 127.79, 128.49, 128.97, 130.25, 130.55, 132.89, 133.76, 135.58, 136.36, 149.87, 150.52, 169.61. MS APCI: 384/386 (P+1, parent, Cl$^{35}$/Cl$^{37}$).

EXAMPLE 2

3-(4-Chloro-phenyl)-1-[8-(4-methyl-piperazin-1-yl)-3,4-dihydro-1H-isoquinolin-2-yl]-propan-1-one: Prepared according to Example 1, mp 84° C., in 74% yield.

$^{13}$C-NMR (δ, CDCl$_3$): 28.76, 29.91, 30.74, 31.07, 35.49, 35.58, 40.35, 40.86, 43.32, 43.87, 46.16, 46.34, 52.28, 52.51, 55.60, 55.91, 117.89, 118.13, 123.73, 124.53, 127.43, 127.81, 128.70, 128.76, 129.22, 129.96, 130.01, 132.04, 135.81, 136.63, 140.11, 149.82, 150.44, 170.99, 173.11. MS APCI: 398/400 (P+1, parent, Cl$^{35}$/Cl$^{37}$). Anal. Calc'd for C$_{23}$H$_{28}$ClN$_3$O.HCl.H$_2$O: C, 61.06; H, 6.91; N, 9.29. Found: C, 61.15; H, 6.87; N, 9.13.

EXAMPLE 3

2-(4-Methoxy-phenyl)-1-[8-(4-methyl-piperazin-1-yl)-3,4-dihydro-1H-isoquinolin-2-yl]-ethanone: Prepared according to Example 1, mp 63° C., in 76% yield.

$^{13}$C-NMR (δ, CDCl$_3$): 28.76, 29.91, 30.74, 31.07, 35.49, 35.58, 40.35, 40.86, 43.32, 43.87, 46.16, 46.34, 52.28, 52.51, 55.60, 55.91, 117.89, 118.13, 123.73, 124.53, 127.43, 127.81, 128.70, 128.76, 129.22, 129.96, 130.01, 132.04, 135.81, 136.63, 140.11, 149.82, 150.44, 170.99, 173.11. MS APCI: 380 (P+1, parent). Anal. Calc'd for C$_{23}$H$_{29}$ClN$_3$O$_2$.HCl.2H$_2$O: C, 61.12; H, 7.58; N, 9.30. Found: C, 61.27; H, 7.58; N, 9.50.

EXAMPLE 4

1-[8-(4-Methyl-piperazin-1-yl)-3,4-dihydro-1H-isoquinolin-2-yl]-2-p-tolyl-ethanone: Prepared according to Example 1 in 96% yield.

$^{13}$C-NMR (δ, CDCl$_3$): 28.76, 29.91, 30.74, 31.07, 35.49, 35.58, 40.35, 40.86, 43.32, 43.87, 46.16, 46.34, 52.28, 52.51, 55.60, 55.91, 117.89, 118.13, 123.73, 124.53, 127.43, 127.81, 128.70, 128.76, 129.22, 129.96, 130.01, 132.04, 135.81, 136.63, 140.11, 149.82, 150.44, 170.99, 173.11. MS APCI: 364 (P+1. parent). Anal. Calc'd for C$_{23}$H$_{29}$N$_3$O.HCl.2H$_2$O: C, 63.36; H, 7.86; N, 9.64. Found: C, 63.73; H, 7.72; N, 9.82.

EXAMPLE 5

2-(4-Chloro-phenoxy)-1-[8-(4-methyl-piperazin-1-yl)-3,4-dihydro-1H-isoquinolin-2-yl]-ethanone: Prepared according to Example 1 in 100% yield.

$^{13}$C-NMR (δ, CDCl$_3$): 28.52, 30.01, 40.83, 41.44, 43.01, 43.32, 46.22, 52.37, 52.49, 55.61, 55.70, 68.14, 68.33, 116.09, 117.97, 118.40, 123.99, 124.42, 126.76, 127.54, 127.93, 128.40, 128.62, 129.71, 135.50, 136.29, 149.88, 150.60, 156.78, 166.65, 166.80. MS APCI: 400/402 (P+1. parent, Cl$^{35}$/Cl$^{37}$). Anal. Calc'd for C$_{22}$H$_{26}$ClN$_3$O$_2$.HCl.7/4H$_2$O: C, 56.47; H, 6.57; N, 8.98. Found: C, 56.43; H, 6.48; N, 8.44.

EXAMPLE 6

2-(2,4-Dichloro-phenyl)-1-[8-(4-methyl-piperazin-1-yl)-3,4-dihydro-1H-isoquinolin-2-yl]-ethanone: Prepared according to Example 1, mp 85° C., in 100% yield.

$^{13}$C-NMR (δ, CDCl$_3$): 28.74, 29.96, 37.94, 38.47, 40.61, 41.24, 43.70, 44.37, 46.21, 46.31, 52.34, 52.44, 55.61, 55.66, 76.94, 77.26, 77.58, 117.89, 118.19, 123.74, 124.47, 127.40, 127.46, 127.81, 128.38, 129.03, 129.35, 131.28, 132.18, 132.25, 132.32, 133.45, 134.69, 134.93, 135.61, 136.38, 149.98, 150.54, 168.69, 168.79. MS APCI: 418/420/422 (P+1, parent Cl$^{35}$/Cl$^{37}$). Anal. Calc'd for C$_{22}$H$_{25}$Cl$_2$N$_3$O.HCl.2H$_2$O: C, 53.83; H, 6.16; N, 8.56. Found: C, 53.77; H, 6.18; N, 8.37.

EXAMPLE 7

2-(2-Chloro-phenyl)-1-[8-(4-methyl-piperazin-1-yl)-3,4-dihydro-1H-isoquinolin-2-yl]-ethanone: Prepared according to Example 1, mp 54° C., in 66% yield.

$^{13}$C-NMR (δ, CDCl$_3$): 28.81, 29.96, 38.57, 39.13, 40.46, 41.28, 43.69, 44.42, 46.23, 46.30, 52.34, 52.40, 55.63, 117.93, 118.16, 123.79, 124.49, 127.19, 127.38, 127.68, 128.37, 128.54, 129.16, 129.58, 130.25, 131.19, 133.57, 135.68, 136.40, 149.99, 150.56, 169.23. MS APCI: 384/386 (P+1, parent Cl$^{35}$/Cl$^{37}$). Anal. Calc'd for C$_{22}$H$_{26}$ClN$_3$O.HCl.H$_2$O: C, 60.27; H, 6.67; N, 9.58. Found: C, 60.37; H, 6.57; N, 9.44.

EXAMPLE 8

2-Cyclopropyl-1-[8-(4-methyl-piperazin-1-yl)-3,4-dihydro-1H-isoquinolin-2-yl]-ethanone: Prepared according to Example 1, mp 66° C., in 78% yield.

$^{13}$C-NMR (δ, CDCl$_3$): 4.71, 4.76, 7.36, 7.46, 28.82, 30.07, 39.16, 39.31, 40.22, 40.85, 43.40, 43.88, 46.21, 46.37, 52.31, 52.55, 55.63, 55.95, 117.92, 118.09, 123.75, 124.51, 127.30, 127.71, 128.94, 129.39, 135.74, 136.82, 150.52, 171.82. MS APCI: 314 (parent, P+1). Anal. Calc'd for C$_{19}$H$_{27}$N$_3$O.HCl.2H$_2$O: C, 59.13; H, 8.36; N, 10.89. Found: C, 59.51; H, 8.48; N, 10.89.

EXAMPLE 9

1-[8-(4-Methyl-piperazin-1-yl)-3,4-dihydro-1H-isoquinolin-2-yl]-2-pyridin-3-yl-ethanone: Prepared according to Example 1, mp 56° C.

$^{13}$C-NMR (δ, CDCl$_3$): 28.62, 29.91, 38.19, 38.76, 40.61, 41.18, 43.80, 44.34, 46.21, 46.37, 52.37, 52.49, 55.60, 55.91, 117.97, 118.20, 123.63, 123.71, 124.57, 127.51, 127.86, 128.33, 128.92, 131.03, 136.29, 136.53, 137.07, 148.43, 148.51, 150.20, 150.39, 150.55, 169.05, 169.12. MS APCI: 351 (parent, P+1). Anal. Calc'd for C$_{21}$H$_{24}$N$_4$O.2HCl.9/4H$_2$O: C, 53.85; H, 7.10; N, 11.96. Found: C, 54.40; H, 7.08; N, 11.91.

EXAMPLE 10

(4-Chloro-phenyl)-[8-(4-methyl-piperazin-1-yl)-3,4-dihydro-1H-isoquinolin-2-yl]-methanone: Prepared according to Example 1, mp 52° C., in 55% yield.

$^{13}$C-NMR (δ, CDCl$_3$): 28.44, 41.23, 42.06, 46.20, 52.30, 55.57, 117.84, 124.26, 128.01, 128.88, 135.02. MS APCI: 370/372 (parent, P+1, Cl$^{35}$/Cl$^{37}$). Anal. Calc'd for C$_{21}$H$_{24}$Cl$_2$N$_3$O.HCl.2H$_2$O: C, 57.02; H, 6.61; N, 9.50. Found: C, 36.95; H, 6.35; N, 9.08.

EXAMPLE 11

[8-(4-Methyl-piperazin-1-yl)-3,4-dihydro-1H-isoquinolin-2-yl]-(4-morpholin-4-yl-phenyl)-methanone: Prepared according to Example 1, mp 129° C. (dec.), in 49% yield.

$^{13}$C-NMR (δ, CDCl$_3$): 46.30, 48.79, 52.35, 55.67, 66.94, 114.64, 118.02, 124.29, 127.15, 127.49, 129.07, 129.34, 152.42. MS APCI: 421 (parent, P+1).

EXAMPLE 12

2-(3,4-Dichloro-phenyl)-1-[8-(4-methyl-piperazin-1-yl)-3,4-dihydro-1H-isoquinolin-2-yl]-ethanone: Prepared according to Example 1, mp 66° C., in 63% yield.

$^{13}$C-NMR (δ, CDCl$_3$): 28.64, 29.91, 40.19, 40.57, 40.88, 41.17, 43.81, 44.46, 46.19, 46.35, 52.33, 52.50, 55.60, 55.92, 117.95, 118.23, 123.73, 124.63, 127.52, 127.89, 128.33, 128.80, 130.66, 130.70, 130.89, 131.29, 135.40, 136.28, 149.85, 150.52, 168.98, 173.10. MS APCI: 418/420/422 (parent, P+1, Cl$^{35}$/Cl$^{37}$).

EXAMPLE 13

2-(4-Chloro-benzenesulfonyl)-8-(4-methyl-piperazin-1-yl)-1,2,3,4-tetrahydro-isoquinoline: Prepared according to Example 1, in 68% yield.

$^{13}$C-NMR (δ, CDCl$_3$): 29.04, 43.80, 44.58, 46.31, 52.44, 55.75, 118.18, 124.56, 127.60, 127.67, 129.15, 129.43, 134.58, 135.72, 139.43, 150.19. MS APCI: 406/408 (parent, P+1, Cl$^{35}$/Cl$^{37}$).

The invention claimed is:

1. A compound of the formula

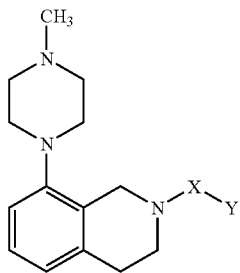

I wherein X is a linker group selected from the group consisting of CH$_2$, CH$_2$CH$_2$, C=O, C=OCH$_2$, CH$_2$C=O, OCH$_2$, OCH$_2$CH$_2$, CH$_2$O, and CH$_2$CH$_2$O, and Y is an alkyl or aryl group,
  wherein the aryl group is selected from phenyl, or pyridyl;
  wherein the phenyl may be optionally substituted with one or more substituents independently selected from halogen, trifluoromethyl, OR$_2$, morpholinyl, 2-oxo-oxazolidin-3-yl or 2-oxo-pyrrolidin-1-yl;
  wherein R$_2$ is selected from the group consisting of alkyl and C$_6$–C$_{14}$ aryl.

2. A compound according to claim 1 wherein the aryl group is phenyl having a para substituent selected from bromine, trifluoromethyl, 2-oxo-oxazolidin-3-yl or 2-oxo-pyrrolidin-1-yl.

3. A compound selected from:
  N-(4-Chlorophenylacetyl)-8-(4-methylpiperazinyl)-tetrahydroisoquinoline;
  3-(4-Chloro-phenyl)-1-[8-(4-methyl-piperazin-1-yl)-3,4-dihydro-1H-isoquinolin-2-yl]-propane-1-one;
  2-(4-Methoxy-phenyl)-1-[8-(4-methyl-piperazin-1-yl)-3,4-dihydro-1H-isoquinolin-2-yl]-ethanone;
  1-[8-(4-Methyl-piperazin-1-yl)-3,4-dihydro-1H-isoquinolin-2-yl]-2-p-tolyl-ethanone;
  2-(4-Chloro-phenoxy)-1-[8-(4-methyl-piperazin-1-yl)-3,4-dihydro-1H-isoquinolin-2-yl]-ethanone;
  2-(2,4-Dichloro-phenyl)-1-[8-(4-methyl-piperazin-1-yl)-3,4-dihydro-1H-isoquinolin-2-yl]-ethanone;
  2-(2-Chloro-phenyl)-1-[8-(4-methyl-piperazin-1-yl)-3,4-dihydro-1H-isoquinolin-2-yl]-ethanone;
  2-Cyclopropyl-1-[8-(4-methyl-piperazin-1-yl)-3,4-dihydro-1H-isoquinolin-2-yl]-ethanone;
  1-[8-(4-Methyl-piperazin-1-yl)-3,4-dihydro-1H-isoquinolin-2-yl]-2-pyridin-3-yl-ethanone;
  (4-Chloro-phenyl)-[8-(4-methyl-piperazin-1-yl)-3,4-dihydro-1H-isoquinolin-2-yl]-methanone;
  [8-(4-Methyl-piperazin-1-yl)-3,4-dihydro-1H-isoquinolin-2-yl]-(4-morpholin-4-yl-phenyl)-methanone;
  2-(3,4-Dichloro-phenyl)-1-[8-(4-methyl-piperazin-1-yl)-3,4-dihydro-1H-isoquinolin-2-yl]-ethanone; and
  2-(4-Chloro-benzenesulfonyl)-8-(4-methyl-piperazin-1-yl)-1,2,3,4-tetrahydroisoquinoline.

4. A method of treating a disorder or condition in a mammal selected from the group consisting of anxiety, depression, dysthymia, major depressive disorder, migraine, post-traumatic stress disorder, avoidant personality disorder, borderline personality disorder and phobias, comprising administering to a mammal in need of such treatment an effective amount of a compound wherein the compound is selected from:
  N-(4-Chlorophenylacetyl)-8-(4-methylpiperazinyl)-tetrahydroisoquinoline;
  3-(4-Chloro-phenyl)-1-[8-(4-methyl-piperazin-1-yl)-3,4-dihydro-1H-isoquinolin-2-yl]-propan-1-one;
  2-(4-Methoxy-phenyl)-1-[8-(4-methyl-piperazin-1-yl)-3,4-dihydro-1H-isoquinolin-2-yl]-ethanone;
  1-[8-(4-Methyl-piperazin-1-yl)-3,4-dihydro-1H-isoquinolin-2-yl]-2-p-tolyl-ethanone;
  2-(4-Chloro-phenoxy)-1-[8-(4-methyl-piperazin-1-yl)-3,4-dihydro-1H-isoquinolin-2-yl]-ethanone;
  2-(2,4-Dichloro-phenyl)-1-[8-(4-methyl-piperazin-1-yl)-3,4-dihydro-1H-isoquinolin-2-yl]-ethanone;
  2-(2-Chloro-phenyl)-1-[8-(4-methyl-piperazin-1-yl)-3,4-dihydro-1H-isoquinolin-2-yl]-ethanone;
  2-Cyclopropyl-1-[8-(4-methyl-piperazin-1-yl)-3,4-dihydro-1H-isoquinolin-2-yl]-ethanone;
  1-[8-(4-Methyl-piperazin-1-yl)-3,4-dihydro-1H-isoquinolin-2-yl]-2-pyridin-3-yl-ethanone;
  (4-Chloro-phenyl)-[8-(4-methyl-piperazin-1-yl)-3,4-dihydro-1H-isoquinolin-2-yl]-methanone;
  [8-(4-Methyl-piperazin-1-yl)-3,4-dihydro-1H-isoquinolin-2-yl]-(4-morpholin-4-yl-phenyl)-methanone;
  2-(3,4-Dichloro-phenyl)-1-[8-(4-methyl-piperazin-1-yl)-3,4-dihydro-1H-isoquinolin-2-yl]-ethanone; and
  2-(4-Chloro-benzenesulfonyl)-8-(4-methyl-piperazin-1-yl)-1,2,3,4-tetrahydroisoquinoline.

* * * * *